(12) United States Patent
Cavaliero et al.

(10) Patent No.: US 9,341,600 B2
(45) Date of Patent: May 17, 2016

(54) DEFLECTION GAUGE FOR FLOOR TEST APPARATUS

(71) Applicant: UNITED STATES GYPSUM COMPANY, Chicago, IL (US)

(72) Inventors: Robert W. Cavaliero, Mundelein, IL (US); Robert Peddle, Lake Villa, IL (US)

(73) Assignee: UNITED STATES GYPSUM COMPANY, Chicago, IL (US)

( * ) Notice: Subject to any disclaimer, the term of this patent is extended or adjusted under 35 U.S.C. 154(b) by 0 days.

(21) Appl. No.: 14/507,263

(22) Filed: Oct. 6, 2014

(65) Prior Publication Data

US 2015/0226623 A1    Aug. 13, 2015

Related U.S. Application Data

(60) Provisional application No. 61/937,172, filed on Feb. 7, 2014.

(51) Int. Cl.
*G01N 3/00* (2006.01)
*G01N 29/11* (2006.01)
(Continued)

(52) U.S. Cl.
CPC  *G01N 29/11* (2013.01); *G01L 1/04* (2013.01); *G01L 9/0001* (2013.01); *G01N 3/00* (2013.01);
(Continued)

(58) Field of Classification Search
CPC ........ G01L 1/04; G01L 9/0001; G01N 19/04; G01N 2203/0005; G01N 2203/0062; G01N 2203/0073; G01N 2291/015; G01N 2291/0232; G01N 29/11; G01N 3/00; G01N 3/08

USPC ................... 73/818, 760, 763, 862.451, 1.13; 177/170, 171, 225, 256
See application file for complete search history.

(56) References Cited

U.S. PATENT DOCUMENTS 2,066,311 A    1/1937    Appel et al.
2,969,669 A    1/1961    Hirschhorn
(Continued)

FOREIGN PATENT DOCUMENTS

CN    101413873    4/2009
CN    201765174    3/2011
(Continued)

OTHER PUBLICATIONS

Fiore, Marina, "Laminam 5—Robinson Test (ASTM C627)," Test Apparatus and interpretation of the results, Jan. 24, 2014, retrieved from internet <http://www.laminam.pl/certyfikaty/Laminam%205%20-%20Robinson%20Test.pdf> on May 21, 2015, pp. 1-4.
(Continued)

*Primary Examiner* — Lisa Caputo
*Assistant Examiner* — Jonathan Dunlap
(74) *Attorney, Agent, or Firm* — Greer, Burns & Crain, Ltd.; Pradip Sahu; Philip T. Petti

(57) ABSTRACT

A deflection gauge configured for use with a floor test apparatus is provided. The gauge includes a housing, a string potentiometer mounted on the housing, and a channel extending from the housing and pivotably supporting a pivot beam. The pivot beam has a contact button at one end and an attachment point on an opposite end configured for receiving a string of the potentiometer. Deflection of the contact button due to floor sample weight stresses causes the attachment point to pivot and cause linear extension of the string, which is measured by the potentiometer.

11 Claims, 3 Drawing Sheets

(51) Int. Cl.
*G01L 1/04* (2006.01)
*G01L 9/00* (2006.01)
*G01N 3/08* (2006.01)
*G01N 19/04* (2006.01)

(52) U.S. Cl.
CPC .............. *G01N 3/08* (2013.01); *G01N 19/04* (2013.01); *G01N 2203/0005* (2013.01); *G01N 2203/0062* (2013.01); *G01N 2203/0073* (2013.01); *G01N 2291/015* (2013.01); *G01N 2291/0232* (2013.01)

(56) References Cited

U.S. PATENT DOCUMENTS

| | | | |
|---|---|---|---|
| 3,102,414 A | 9/1963 | Wharff, Jr. | |
| 3,404,556 A | 10/1968 | Kameras | |
| 3,426,853 A * | 2/1969 | Rosso Del | G01G 19/22 177/103 |
| 3,641,807 A | 2/1972 | Brooks | |
| 3,724,574 A * | 4/1973 | Hutchinson | A61B 5/1072 177/210 R |
| 4,039,036 A * | 8/1977 | Baumgartner | G01G 7/04 177/185 |
| 4,052,888 A * | 10/1977 | Brown | A61B 8/00 73/625 |
| 4,569,222 A | 2/1986 | Arnold et al. | |
| 5,563,329 A | 10/1996 | Smith et al. | |
| 5,616,848 A | 4/1997 | Hemingway et al. | |
| 5,998,742 A * | 12/1999 | Liu | G01G 7/02 177/184 |
| 6,244,108 B1 * | 6/2001 | McInnes | G01M 1/02 73/462 |
| 6,284,987 B1 * | 9/2001 | Al-Modiny | F17C 13/023 177/170 |
| 2002/0074169 A1 * | 6/2002 | Al-Modiny | F17C 13/023 177/1 |

FOREIGN PATENT DOCUMENTS

| | | |
|---|---|---|
| GB | 325358 | 2/1930 |
| JP | 09184797 | 7/1997 |
| JP | 09325112 | 12/1997 |
| JP | 11153539 | 6/1999 |

OTHER PUBLICATIONS

Partial Search from International Patent Application No. PCT/US2015/014591, dated May 29, 2015.

* cited by examiner

DEFLECTION GAUGE FOR FLOOR TEST APPARATUS

RELATED APPLICATION

This application claims 35 USC 119(e) priority based on U.S. Provisional Patent Application No. 61/937,172 filed Feb. 7, 2014.

BACKGROUND

The present invention relates generally to floor test devices, commonly referred to as Robinson-Type floor testers, and more specifically to such an apparatus with a positive drive system and an updated base structure.

Conventional floor system durability tests are conducted under ASTM standards. Specifically ASTM C627-10 test standard, adopted in 1968, calls for the use of a test stand providing an elevated base beneath which is located an electric motor drive system, with a vertically extending drive shaft projecting through an opening in the base and having a coupler. A target floor system to be tested, usually a ceramic tile grouted floor system and associated underlayment, is placed upon the base, and has an opening for receiving the coupling and part of the shaft. A wheeled, platform-like carriage is placed upon the floor sample, with the wheels in contact with an upper surface of the sample. The above-described Robinson-Type floor test apparatus operates by test personnel incrementally adding weight to the carriage for 900 rotational cycles at each weight setting. At some point, sufficient weight is added until a designated amount of cracks appear in the floor, designating floor failure.

There is a desire in the floor system production industry for improving the operation of the conventional Robinson-Type floor test apparatus. One drawback of the current device is that due to the established drive system, operating through chain and sprocket is more prone to wear, requires frequent maintenance, and the existing motor technology combines to create a situation where the prescribed 15 RPM of the carriage is not consistently met over extended operational periods. Also, the conventional base has been found to be relatively sensitive to damage from vibration. Thus, there is a need for a floor test apparatus that addresses the drawbacks of the conventional Robinson-Type device.

SUMMARY

The above-identified needs are met by the present improved floor test apparatus, featuring a positive, direct shaft drive system with an enhanced control system that reduces variations in output RPMs. In the preferred embodiment, the control system includes a programmable logic controller (PLC) and a variable frequency drive having a feedback signal. In addition, the base features an embedded steel framework that defines channels receiving the shaft and drive components, reinforces the concrete and also provides enhanced support for the concrete base substrate. As such, the present base is comparatively more resistant to vibration damage than conventional bases. A main, generally vertical channel accommodates a vertical drive shaft and a bevel gear box. In addition, a supplemental, generally horizontal channel is in communication with the main channel and receives at least a portion of the main horizontal drive shaft, which is ultimately connected to the drive motor. Further, the present electric drive motor has the above-identified PLC that more accurately matches drive shaft output to ASTM prescribed ranges.

More specifically, a floor test apparatus is provided, including a base having an upper surface and defining an output shaft opening, a frame disposed in the base, having a main vertically projecting channel in communication with a supplemental, generally horizontally projecting channel having an access opening in a sidewall of the base. A main drive shaft passes through the supplemental channel and is coupled to a gearbox disposed in the main channel. A secondary shaft projects generally vertically from the gearbox and is connected for common rotation with the main drive shaft.

In another embodiment, a floor test apparatus is provided, including a base having an upper surface and defining an output shaft opening, a frame disposed in the base, having a main vertically projecting channel in communication with a supplemental, generally horizontally projecting channel having an access opening in a sidewall of the base. A main drive shaft passes through the supplemental channel and is coupled to a gearbox disposed in the main channel. A secondary shaft projects generally from the gearbox and is connected for common rotation with the main drive shaft. A cover plate receives an end of the secondary shaft and is mounted to an upper end of the channel. The upper end of the channel defines a recessed seat for said cover plate, and at least one of the main channel and the supplemental channel are provided with externally projecting tabs for enhancing connection to poured concrete forming the base.

In still another embodiment, a deflection gauge configured for use with a floor test apparatus is provided. The gauge includes a housing, a string potentiometer mounted on the housing, and a channel extending from the housing and pivotably supporting a pivot beam. The pivot beam has a contact button at one end and an attachment point on an opposite end configured for receiving a string of the potentiometer. Deflection of the contact button due to floor sample weight stresses causes the attachment point to pivot and cause linear extension of the string, which is measured by the potentiometer.

DETAILED DESCRIPTION

Figure 1:
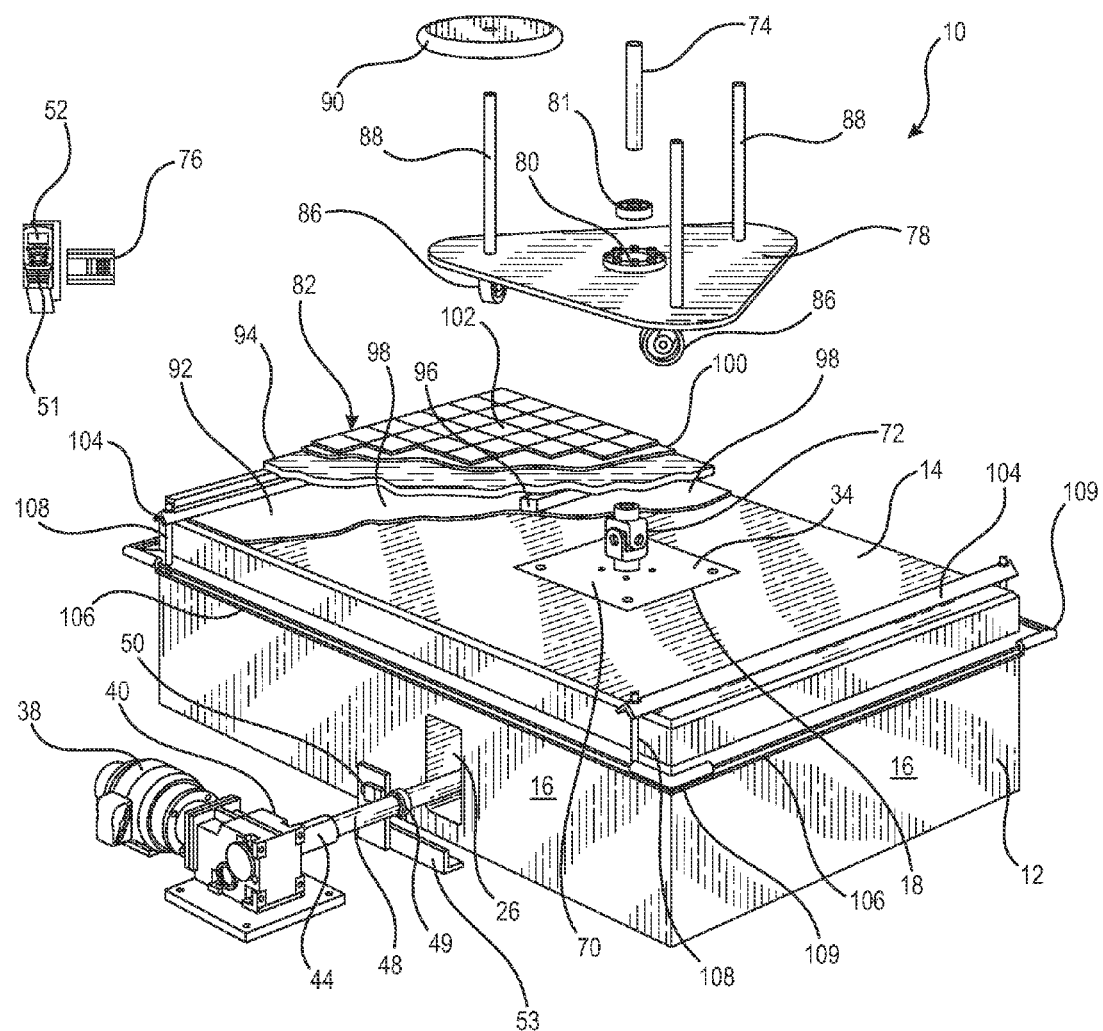
FIG. 1 is a perspective elevation of the present floor testing apparatus.
Figure 2:
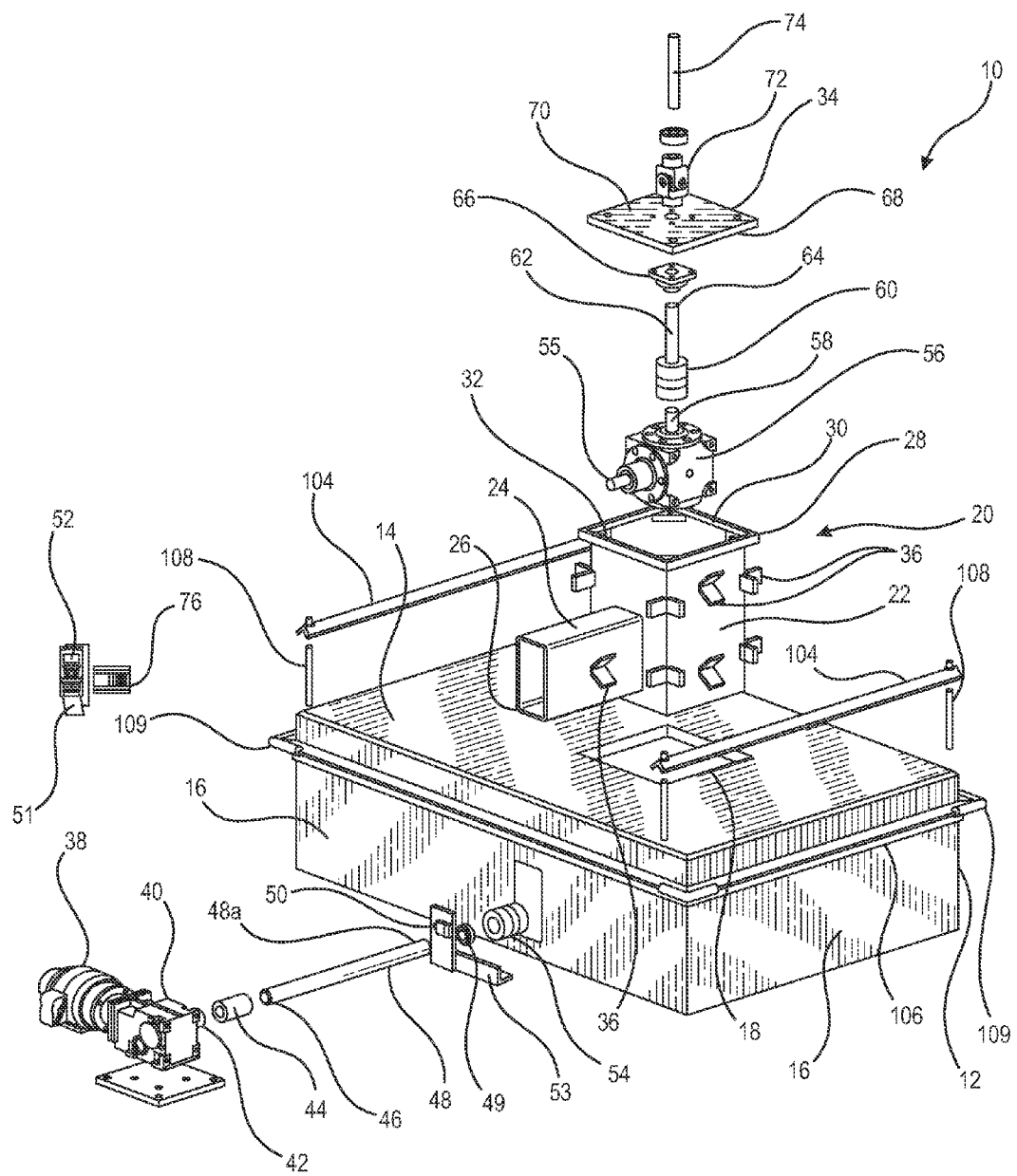
FIG. 2 is an exploded perspective view of the present floor testing apparatus.

Referring to FIGS. 1 and 2, the present floor testing apparatus is generally designated 10. The present apparatus 10 is basically similar to, but features several performance enhancements over the conventional Robinson-Type test apparatus. Included on the apparatus 10 is a generally block-shaped base 12, primarily fabricated of poured concrete, and including an upper surface 14 and a plurality of sidewalls 16. To accommodate floor system test samples, which conventionally measure 4 feet in length×4 feet in width, the base 12 is contemplated as providing the upper surface 14 with at least that area, and preferably a larger area, such as 4 feet×6 feet, depending on the application, so that the entire floor sample is accommodated. A feature of the base 12 is that an output shaft opening 18 is defined in the upper surface 14, and is non-centrally located on that surface, as seen in FIG. 1. Also, while other shapes are contemplated, the output shaft opening 18 is preferably polygonal, and most preferably square or rectangular.

One feature of the present apparatus 10 is that the base is provided with a frame, generally designated 20. It is preferred that the frame 20 is cast into the poured concrete base 12. Included on the frame 20 is a main, vertically projecting tubular channel 22 in communication with a supplemental, generally horizontally projecting tubular channel 24. In the preferred embodiment, the main channel 22 has a cross-sectional area that is greater than a similar cross-sectional area of the supplemental channel 24. The supplemental channel 24 has an access opening 26 flush with a sidewall 16a of the base. Also, an upper end 28 of the main channel 22 includes a polygonal frame 30 defining a recessed seat 32. The recessed seat 32 is dimensioned for receiving a cover plate 34 that, when mounted, is flush with the upper surface 14 of the base 12. Another feature of the frame 20 is that at least one of the main channel 22 and the supplemental channel 24 are provided with externally projecting tabs 36 for enhancing connection to poured concrete forming the base 12. While other configurations are contemplated, the tabs 36 preferably form one of a general "V" or "L" shape when viewed from one of the top or sides. It will be understood that the frame 20 also reinforces the poured concrete forming the base 12.

Also included on the apparatus 10 is a motor 38, preferably an electric motor of suitable power, preferably an AC motor producing on the order of 1.5 HP. The type and size of the motor 38 may vary to suit the application. In the preferred embodiment, the motor 38 is located externally of the base 12. To reduce the motor RPM's so that a final desired 15 RPM rotation of a test carriage is achieved, connected to the motor 38 is a gear reducer 40. The gear reducer 40 has specifications that may vary to suit the situation, but in the preferred embodiment, a Dodge 107.47:1 gear reducer provides an approximate 16 RPM, a programmable logic controller and a variable frequency drive controller, both described below provide further reduction for achieving and maintaining the ASTM specified 15+/−0.5 RPM during the floor testing operation. Ultimately, a preferred 107.47:1 reduction of motor output is obtained by the gear reducer 40.

An output shaft 42 (FIG. 2) of the gear reducer 40 is connected via a coupling 44 to a first end 46 of a main drive shaft 48, generally horizontally oriented in the present apparatus 10. In the preferred embodiment, the drive shaft 48 is keyed to better fit in the coupling 44, preferably of the solid steel type, so that the shaft rotates with the output shaft 42. Just beyond the steel coupling 44, and between the coupling and the access opening 26 a shaft-collar eccentric cam 49 is mounted on the shaft 48, and rotation of the shaft causes the eccentric cam to trigger a limit switch 50. The limit switch 50 provides a single low-voltage pulse to a Programmable Logic Controller (PLC) 51 preferably having a front panel display 52 for monitoring of each revolution of a shaft and a steel carriage (described below) during testing. In the preferred embodiment, the limit switch 50 is attached to a fabricated bracket 53, which is preferably anchored to the floor that also supports the base 12, however other mounting locations are contemplated. Other shaft rpm measuring systems are also contemplated, but they need to be sufficiently durable for operating in the relatively dusty environment of floor testing.

A second coupling, 54 preferably a spider type coupling, connects a second end 48a of the main drive shaft 48 to an input shaft 55 of a gearbox 56. The gearbox 56 is preferably of the bevel type; however other conventional types are contemplated, provided that the input motion is transferred at a designated ratio to an output shaft 58 oriented at 90° to the input shaft 55. In the preferred embodiment, a 1:1 ratio is designated; however other ratios are contemplated depending on the application. Also, the main vertical channel 22 of the frame 20 is dimensioned to accommodate the gearbox 56.

A third coupling 60, also preferably a spider type, connects the bevel gearbox output shaft 58 to a secondary shaft 62 that rotates in common with the main drive shaft 48. An upper end 64 of the secondary shaft 62 is supported by a flanged bearing 66 that is mounted to an underside 68 of the cover plate 34. The secondary shaft 62 is dimensioned to project past an upper surface 70 of the plate 34, which as discussed above, is flush with the upper surface 14 of the base 12.

A U-joint 72 is coupled to the upper shaft end 64, and is in turn connected to a keyed stub shaft 74. Also, another feature of the motor 38 is that it is electrically connected to the PLC 52 and also to a programmable variable frequency drive controller 76 as known in the motor control art for regulating the output of the gear reducer so that the desired 15 RPM of a carriage 78 driven by the stub shaft 74 is obtained. The controller 76 and the PLC 51 are preferably located remotely from the motor 38, such as on a nearby wall. The location of the controller 76 and the PLC 51 may vary to suit the application. As is known in the art, a keyed opening 80 on the carriage 78 matingly accommodates an end of the continuously keyed stub shaft 74 using an internally keyed and externally toothed collar 81 so that the carriage is rotated by rotation of the stub shaft.

In operation, a sample floor system, shown fragmentarily at 82, is placed upon the upper base surface 14 so that an opening in the sample is in registry with the output shaft opening 18. As is known in the art, the opening in the sample is typically smaller than the area of the cover plate 34. The carriage 78 is placed upon the sample floor system 82, and has a plurality of casters or wheels 86 that rotatably engage the floor system. Also provided on the carriage 78 is a plurality of vertically projecting rods 88 constructed and arranged for receiving a supply of weights 90 that are incrementally added to the rods of the carriage in the course of the testing process. When fully supplied with the weights 90, the carriage 78 can weigh 900 pounds. As discussed above, according to ASTM C627, the carriage 78 rotates 900 cycles at each of a plurality of designated weight settings. With each revolution of the carriage 78, the shaft-collar cam 49 makes contact with and closes the limit switch 50, completing a circuit that sends a single low-voltage pulse to update an internal counter in the programmable logic controller 51, which then updates the front panel display 52. After an 'end of cycle' condition is met, the programmable logic controller 51 triggers the variable frequency drive 76 to stop the cycle and resets an internal counter (not shown) and front panel display to zero for the next cycle.

Referring now to FIG. 1, the sample floor system 82 will be described in greater detail. A sample base 92, typically ½ or ¾ inch plywood, is spaced from a floor underlayment board 94 by base supports 96, constructed and arranged to represent floor joists in an actual floor system. In some applications, 4×4 feet by 2 inch thick concrete pads are alternatively used as substrates for test samples, having a 6×6 inch square opening for receiving the drive shaft 62 and the U-joint 72. The supports 96 create a space 98 between the sample base 92 and the underlayment board 94. An acoustical sound attenuation mat is placed directly on top of the plywood and the seams taped tight and primed. Next, a cementitious or gypsum based flooring underlayment is poured on top to a specified thickness. The underlayment is allowed to dry and gain strength for several days to several weeks before a layer of mastic 100 is applied to the underlayment, and a layer of tile and grout 102 are applied upon the mastic 100 as is customary in the floor system art.

A feature of the present floor testing apparatus 10 is an improved mounting apparatus for securing the sample 82 in place for testing. Included in the mounting apparatus are steel angle iron rails 104 for fastening test samples 82 to the top of the concrete base 12. The rails 104 are used in conjunction with a rigid, preferably metal ledge 106, preferably fixed to all sides 16 of the base 12 by being embedded into the wet concrete of the base 12 or using other known fastening technologies. The ledge 106 is provided with spaced openings for receiving fasteners 108 that secure the bars to ledge. Typical fasteners 108 include threaded rods and nuts. The bars 104 are inserted into the space 98 in the floor sample 82 and the fasteners 108 are then tightened to the ledge 106. Thus, the floor sample 82 is clamped to the base 12. In addition, monitoring instrumentation is optionally mounted to the ledge 106. Corner bumpers 109 of relatively resilient material are provided for protecting associated corners of the ledge 106.

Figure 3:
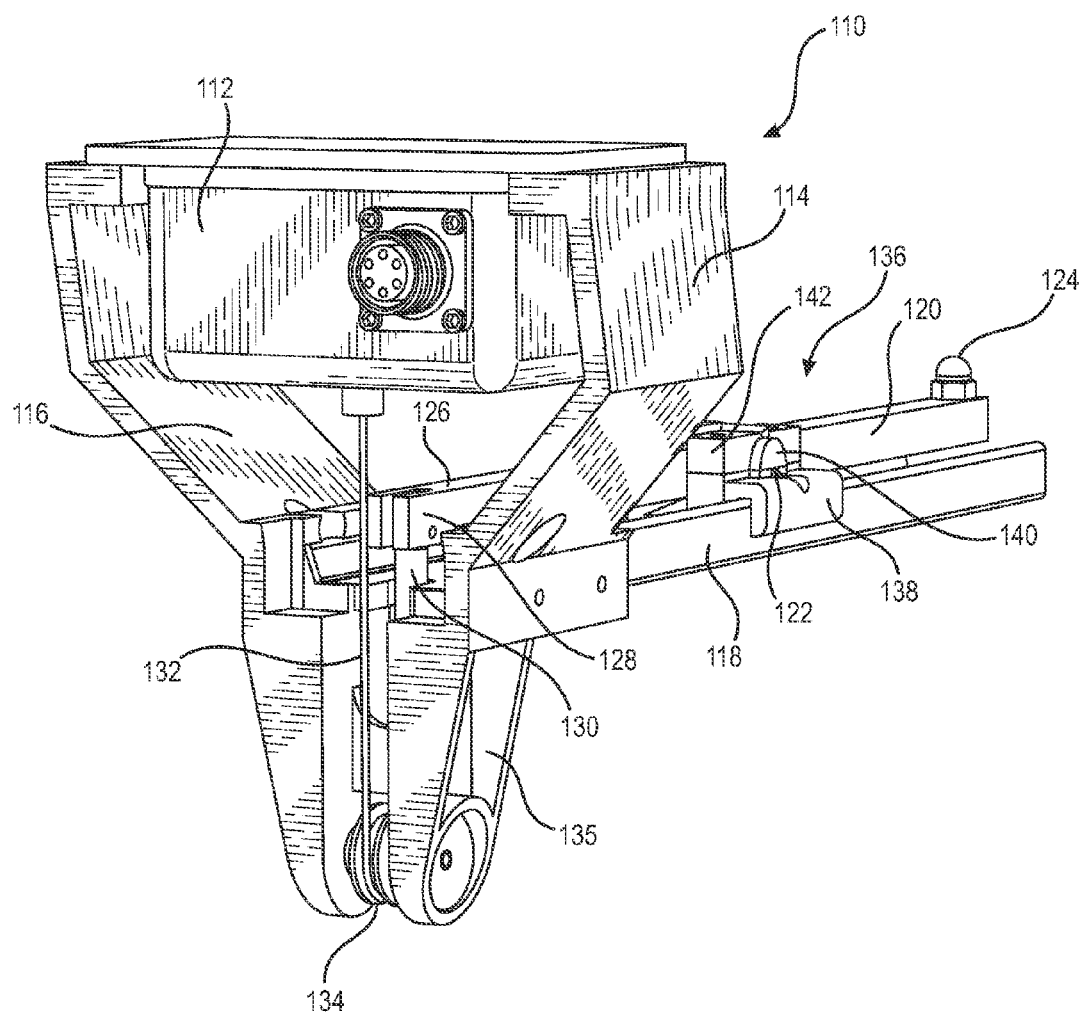
FIG. 3 is a front perspective view of a deflection gauge suitable for use with the present floor testing apparatus.

Referring now to FIG. 3, one of the test instruments used for measuring deflection of the underlayment board 94 is a deflection gauge. Conventional deflection gauges constructed according to ASTM C627 include a lever inserted into the space 98 so that one end of the lever contacts an underside of the underlayment board 94. The lever is maintained in contact with the underlayment board 94 by means of mechanical spring. An opposite end of the lever is connected to a dial gauge. A pivot point is located midway between the first and second ends of the lever, so that deflection of the first end due to the rotation of the weighted carriage will cause a complementary movement of the second end and a reading on the deflection gauge.

Conventional dial indicator displacement transducers are considered less sophisticated than a string potentiometer connected to a data-logging device, in that only the longest deflection is recorded. One drawback is that there is a lack of real-time data of the deflection over time while the carriage 78 is rotating.

To address the drawbacks of the prior art gauges, a deflection gauge is generally designated 110 and has been fabricated to measure positive and negative deflections in the top diaphragm of the test samples which was also designed to be significantly improved from the original ASTM C627 design. A string potentiometer 112 is mounted in a housing 114 of acrylonitrile butadiene styrene (ABS) or equivalent self-supporting, durable materials and is mounted in such a way that it is oriented opposite the direction of the deflections to be measured. The potentiometer 112 is located in a recess 116 of, or otherwise mounted to the housing, which extends perpendicularly to a longitudinal "U"-channel 118. The channel 118 is configured for insertion into the floor sample space 98, and includes a pivot beam 120 attached to the channel at a pivot point 122. A contact button 124 is located at an end of the pivot beam 120 and is constructed and arranged for contacting the underside of the underlayment board 94.

An opposite end 126 of the pivot beam 120 has an attachment point 128 constructed and arranged for accommodating an end 130 of a string 132 of the string potentiometer 112. The tension provided by the string potentiometer 112 to hold the pivot beam 120 taut is used in lieu of the spring mentioned in the original ASTM C627 apparatus design. The string 132 is guided around a pulley 134 rotatably mounted to a pulley mount 135 portion of the housing 114 extending diametrically opposite the housing recess 116 relative to the channel 118, to change the direction the string 132 travels to measure deflections relative to the sample 82. The pulley 134 facilitates movement of the string 132 as the pivot beam 120 pivots due to floor sample movement. Deflection of the contact button 124 due to floor sample weight stresses causes the attachment point 128 to move in the opposite direction, causing linear extension of the string 132, which is measured by the potentiometer 112. Feedback from the string potentiometer 112 is transmitted to a voltage logging device, where slight changes in potential can be converted to precise deflections and used for analysis.

Another feature of the gauge 110 is that the pivot beam 120 is pivotably secured to the channel 118 by a pivot bearing 136 including a bearing base 138 secured to the channel, a transverse pivot axle 140, an internal ball bearing assembly (not shown) and an upper bearing cap 142. The upper bearing cap 142 holds the axle 140 in place on the bearing base 138. Through the use of the present positive, direct drive, which includes the gear reducer 42, the main drive shaft 48, the gearbox 56, the secondary drive shaft 62 and the associated couplings 44, 54 and 60, the present floor apparatus 10 more accurately delivers the targeted 15 RPM of the carriage 78. In addition, the PLC 51 and the programmable controller 76 provides for enhanced operator control over output of the motor 38, and results in a more consistent drive source.

While a particular embodiment of the present positive drive floor test apparatus has been shown and described, it will be appreciated by those skilled in the art that changes and modifications may be made thereto without departing from the invention in its broader aspects and as set forth in the following claims.

What is claimed:

1. A deflection gauge configured for use with a floor test apparatus, comprising:
    a housing;
    a string potentiometer mounted on said housing;
    a channel extending from said housing and pivotably supporting a pivot beam;
    said pivot beam having a contact button at one end and an attachment point on an opposite end configured for receiving a string of said potentiometer, such that deflection of said contact button due to floor sample weight stresses causes said attachment point to cause linear extension of said string, which is measured by said potentiometer; and
    said string potentiometer being constructed and arranged so that said string is disposed for operational movement along an axis generally perpendicular to said pivot beam.

2. The gauge of claim 1, further including a pulley on said housing for facilitating movement of said string in response to pivoting action of said pivot beam, said pulley rotating to accommodate movement of said string as said pivot beam pivots.

3. The gauge of claim 1, further including a bearing associated with said channel for mounting said pivot beam, said bearing including a bearing base secured to said channel, a transverse pivot axle mounted on said base, and an upper bearing cap holding said axle in place on said base.

4. The gauge of claim 3, wherein said bearing is a spherical bearing.

5. The gauge of claim 1, wherein said housing secures said potentiometer and includes a pulley mount that is a mounting point for said pulley around which said string is guided, said housing being constructed and arranged so that said attachment point is located between said pulley and said potentiometer.

6. The gauge of claim 5, wherein said housing holds said string potentiometer in place above said string of said potentiometer.

7. The gauge of claim 1, wherein said channel is constructed and arranged along an axis generally parallel to said pivot beam and said channel has a length approximately coextensive with a length of said pivot beam.

8. A deflection gauge configured for use with a floor test apparatus, comprising:
- a housing;
- a string potentiometer mounted on said housing;
- a channel extending from said housing and pivotably supporting a pivot beam;
- said pivot beam having a contact button at one end and an attachment point on an opposite end configured for receiving a string of said potentiometer, such that deflection of said contact button due to floor sample weight stresses causes said attachment point to cause linear extension of said string, which is measured by said potentiometer.

9. The gauge of claim 8, wherein said housing secures said potentiometer and includes a pulley mount that is a mounting point for a pulley around which said string is guided, said housing being constructed and arranged so that said attachment point is located between said pulley and said potentiometer.

10. The gauge of claim 9, wherein said housing holds said string potentiometer in place above said string of said potentiometer.

11. The gauge of claim 8, wherein said channel is constructed and arranged along an axis generally parallel to said pivot beam and said channel has a length approximately coextensive with a length of said pivot beam.

\* \* \* \* \*